United States Patent [19]

Perren

[11] 4,197,458
[45] Apr. 8, 1980

[54] ELECTRO-OPTICAL APPARATUS FOR THE DETECTION OF THE PRESENCE OF LIQUID

[76] Inventor: Benno Perren, Austrasse 33, 5430 Wettingen, Switzerland

[21] Appl. No.: 929,850

[22] Filed: Jul. 31, 1978

[51] Int. Cl.² ............................................. G01J 1/00
[52] U.S. Cl. .................................................. 250/341
[58] Field of Search ............... 250/338, 341, 343, 344, 250/357

[56] References Cited

U.S. PATENT DOCUMENTS 3,906,232  9/1975  Meihofer ............................. 250/338
4,020,345  4/1977  Meyer ................................. 250/343

Primary Examiner—Alfred E. Smith
Assistant Examiner—Janice A. Howell
Attorney, Agent, or Firm—Werner W. Kleeman

[57] ABSTRACT

An electro-optical apparatus for the detection of the presence of liquid, comprising at least one monochromatic infrared transmitter arranged at the region of a hollow body probe composed of synthetic, high molecular material and totally reflecting the infrared radiation. There are further provided at least one infrared receiver and a circuit for signal processing. The hollow body probe composed of the synthetic, high molecular material or substance is connected by means of a detachable fluidtight connection composed of a further synthetic, high molecular material of the same substance group with a support having at least one hollow chamber or space.

21 Claims, 8 Drawing Figures

ELECTRO-OPTICAL APPARATUS FOR THE DETECTION OF THE PRESENCE OF LIQUID

BACKGROUND OF THE INVENTION

The present invention relates to a new and improved construction of an electro-optical apparatus for the detection of the presence of liquids, which is of the type comprising at least one monochromatic infrared transmitter which is arranged at the region of a hollow body probe composed of a synthetic high molecular substance or material and totally reflecting the infrared radiation, as well as there being provided at least one infrared receiver and a circuit for signal processing.

Such equipment is designated in the art as liquid sensors. In Swiss Pat. No. 512,060 there is taught to the art a compact structural unit which has a high response sensitivity and is extensively non-sensitive to mechanical loads and does not require any subsequent adjustments.

The light-conducting body, used with the prior art equipment, for the detection of the presence of liquid must have high optical transparency, and therefore, in practice is fabricated from acrylic glass.

Owing to the limited resistance of acrylic glass as well as similar light-conducting products with respect to liquids which can be considered to be aggressive, the use of such type liquid sensors is limited as is also their longevity.

All of the heretofore known liquid sensors or feelers additionally require a relatively high transmitting energy of the light-emitting diode, in order to insure for a reproducible response behavior. It is known that for this reason the employment of such type devices, especially the use thereof in conjunction with highly explosive media, is forbidden for reasons of safety in a number of countries.

SUMMARY OF THE INVENTION

Hence, it is a primary object of the present invention to provide a new and improved construction of an electro-optical apparatus for the detection of the presence of liquids which is not associated with the aforementioned drawbacks and limitations of the prior art proposals.

Another and more specific object of the present invention aims at providing a compact construction of an electro-optical apparatus for the detection of also even chemically aggressive liquids, which, additionally, is easy to clean and relatively non-sensitive to contamination and the formation of crust or scale due to crystallization of the liquid and so forth.

A further aspect of the invention aims at providing an electro-optical apparatus for the detection of the presence of liquids which, owing to the low requisite transmitting energy, also can be beneficially utilized in the presence of highly explosive liquids.

Now in order to implement these and still further objects of the invention, which will become more readily apparent as the description proceeds, the hollow body probe or sensor composed of the synthetic, high molecular material or substance is connected by means of a detachable fluidtight connection composed of a further synthetic, high molecular substance of the same material or substance group with a support having at least one hollow space or compartment.

Under the expression synthetic, high molecular substance or material of the same substance or material group as employed herein there is to be understood either identical substances or materials, or, however, substances or materials having the same or at least similar physical properties.

Through the use of selected infrared transmitters in conjunction with the novel hollow body probe it is possible to reduce the transmitting or transmission energy needed for operating the apparatus to less than 30 mW.

BRIEF DESCRIPTION OF THE DRAWINGS

The invention will be better understood and objects other than those set forth above, will become apparent when consideration is given to the following detailed description thereof. Such description makes reference to the annexed drawings wherein.

DETAILED DESCRIPTION OF THE INVENTION

Figure 1:
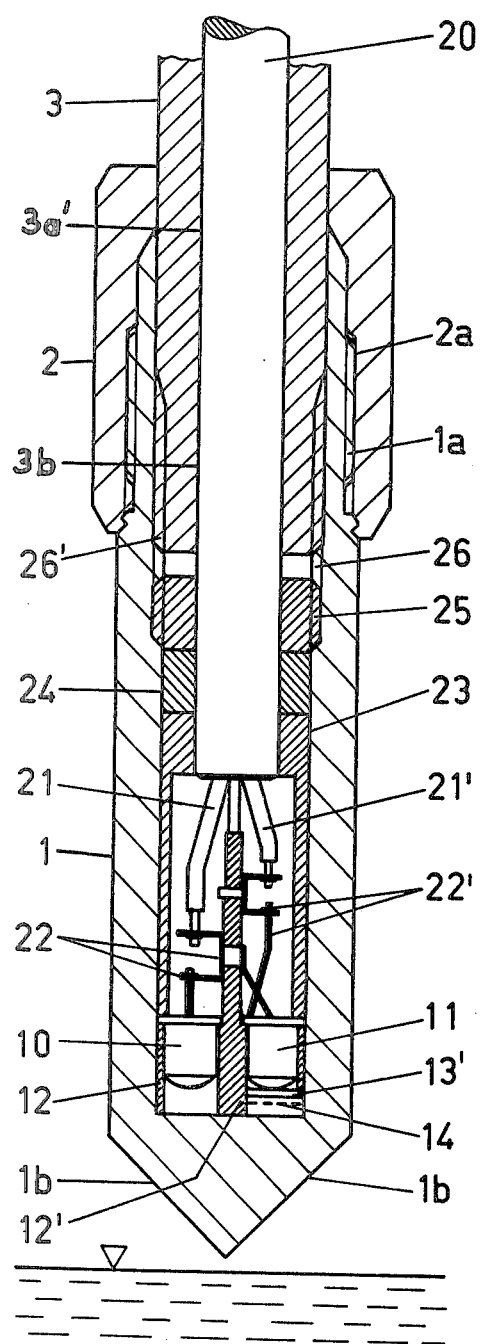
FIG. 1 schematically illustrates a preferred arrangement in an apparatus for the detection of the presence of liquid.

Describing now the drawings, it is to be understood that throughout the various embodiments there have been generally employed the same reference characters to denote the same or analogous components. Turning specifically to the arrangement of FIG. 1 there is designated by reference character 1 a hollow body probe formed of a synthetic, high molecular substance, meaning a polymerized substance, examples of which are illustratively given throughout this disclosure. Threaded onto this hollow body probe 1 is a fluidtight connection 2 in the form of, for instance, a collar or sleeve having internal threads 2a engaging with the external threads 1a of the hollow body probe 1. At least one of the threads 1a or 2a have a substantially cone-shaped core diameter or outer diameter, as the case may be. A tubular carrier or support 3 defining a tubular-shaped body protrudes into the hollow body probe 1 and fixedly retains such at the level of the liquid which is to be monitored. The support 3 has a hollow space or chamber 3a' and its outer surface 3b may be provided with at least one layer or coating of a synthetic, high molecular material of the same substance group as that of the hollow body probe 1.

Internally of the hollow body probe 1 there is located an infrared transmitter 10 and an infrared receiver 11 which are arranged adjacent one another and are centered in a centering sleeve 12 at the region of a totally reflecting boundary surface 1b.

The centering sleeve 12 comprises an intermediate or central web 12' which carries the connections 22 and 22' of the infrared transmitter 10 as well as the infrared receiver 11. At the connections 22 and 22' there are soldered signal lines or conductors 21 and 21', respectively, of a signal cable. This signal cable 20 leads to a not further illustrated conventional circuit for signal processing having standard devices for signal monitoring and optical and acoustical signal indicators or equivalent structure.

The simple assembly of the apparatus which, when necessary, for instance during repair work, can be carried out rapidly, occurs in the following manner.

Figure 1A:
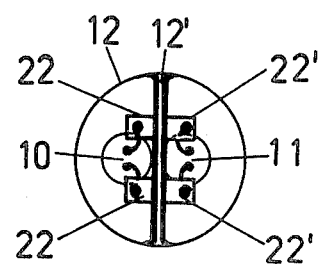
FIG. 1a illustrates details of the current infeed and the assembly of the infrared transmitter and infrared receiver.

The infrared transmitter 10 and the infrared receiver 11 are pressed with a slight pressure—a so-called "push fit"—into the centering sleeve 12 formed of plastic, and the connections or terminals 22 and 22' are soldered, these connections being arranged in the manner apparent by referring to FIGS. 1 and 1a . Thereafter, there are pushed onto the free end of the signal cable 20 the tubular-shaped carrier or support 3, the connection element or connection means 2, a pre-tensioning screw 25 or equivalent structure, a rubber insert 24 and the centering tube 23.

The non-insulated or bare ends of the signal lines 21 and 21' are now appropriately soldered to the upper tabs of the connections 22 and 22', respectively, and the entire unit is pushed into the hollow body probe 1. Internally of the hollow body probe 1 there is provided internal threading or threads 26 at which there can be threaded the pre-tightening or pre-tensioning screw 25 with the aid of a suitable tool until there is obtained a form-locking or positive fixation of all of the elements.

The support or carrier 3 can be now likewise threaded by means of its external threads 26' at the internal threads 26 of the hollow body probe 1. The connection or connection element 2 is threaded by means of its internal threads 2a onto the substantially conical outer threads 1a of the hollow body probe 1, thereby providing a fluidtight connection of the apparatus and basically placing such in a condition where it is ready for use.

The mode of operation of the apparatus is basically known. The infrared transmitter 10 having a LED-diode (for instance of the commercially available type 1A 48 available from the well known Swedish firm ASEA) radiates a monochromatic infrared radiation of 940 nm having a spectral bandwidth 60 nm, which in part is totally reflected at the totally reflecting boundary surface 1b and deflected to the oppositely situated boundary surface. Since at this boundary surface there also occurs a certain total reflection, the infrared receiver 11 which possesses a silicon-PIN-diode (for instance of the type S 138 P available from the well known German firm Telefunken AG) receives an infrared signal.

If the boundary surfaces 1b immerse in a liquid, then the previously described optical transmission path is interrupted, since the infrared radiation now enters the liquid. Now there begins the signal processing. As described in greater detail in my copending U.S. application Ser. No. 929,851, filed July 31, 1978, entitled "Electro-Optical Device For The Detection Of The Presence of Liquid", the disclosure of which is incorporated herein by reference, it is advantageous if at least at the region of the boundary surface which totally reflects the infrared radiation the hollow body probe consists of a halogen-containing polymerizate.

In the embodiment under discussion, all of the parts or components 1, 2 and 3 of the previously described apparatus which come into contact with the liquid or with its vapors are formed of perfluoroalkoxy (PFA).

This affords the tremendous advantage of a non-combustible, chemically resistant apparatus which especially also can be employed in the chemical apparatus industry.

Since the individual parts or components 1, 2 and 3 are exposed to different environmental effects, depending upon the field of application, it is also possible to use a different synthetic, high molecular substance or material. A mutually uniform substance for forming the hollow body probe 1, the connection element 2 and the carrier or support 3 produces the best results as concerns longevity of use or service life of the equipment. Through the combination of substances of the same group of substances, especially with other halogen-containing polymerizates of the same or similar physical properties there are, however, likewise realized satisfactory results.

Due to the use of high molecular substances there is present appreciable scattering at the optical transmission path. This can be somewhat corrected, on the one hand, by the use of passive optical means, such as for instance in FIG. 1, by using a Fresnel lens 13' arranged ahead of the infrared receiver 11 and by means of an infrared filter 14, or, on the other hand, can be reduced by the use of a narrowly focused radiation characteristic of the infrared transmitter 10.

In FIG. 1a the infrared transmitter 10 and the infrared receiver 11 of FIG. 1 have been shown in a top plan view and assembled in the centering sleeve 12. A central or intermediate web 12' at the centering sleeve 12 carries the connections 22 and 22' at which there are soldered or otherwise connected the signal lines 21 and 21', respectively, as well as the corresponding connections at the infrared transmitter 10 and the infrared receiver 11.

According to a further embodiment of the apparatus of this development the intermediate web 12' can be designed as a printed circuit, thereby somewhat reducing the height of the apparatus.

Figure 2:
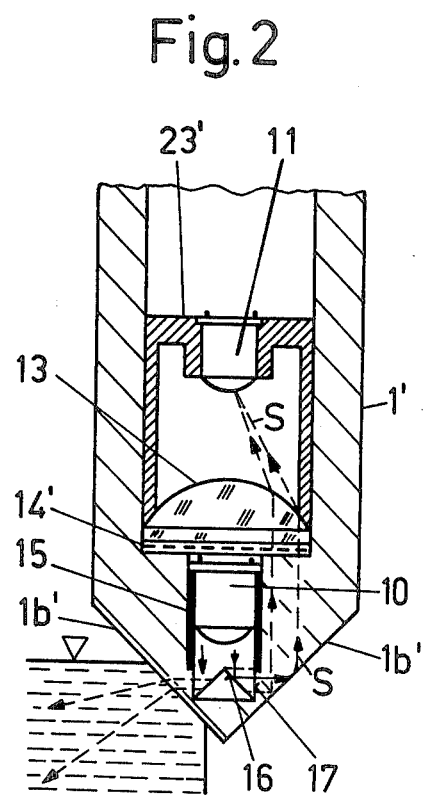
FIG. 2 illustrates in fragmentary sectional view a variant construction of the invention employing tandemly arranged infrared transmitter and infrared receiver.

A further variant of inventive apparatus, as shown in FIG. 2, will be seen to comprise successively or tandemly arranged infrared transmitter 10 and infrared receiver 11. In this embodiment the hollow body probe has been generally designated by reference character 1' and is fabricated from ethylene tetrafluoroethylene (ETFE). At the region of the totally reflecting boundary surfaces 1b' there is centrally provided a bore 17 in which there is mounted an infrared transmitter 10 (GaAs PN-diode, obtainable as commercial type 1A 48 from the firm ASEA) which is surrounded at its outer surface by a metallic absorber tube 15 or equivalent structure which protrudes past the infrared transmitter 10. At the end of the bore 17 there is anchored a metallic deflection cone 16. Above the bore 17 there is located an infrared filter 14', an optical lens 13 as well as a centering tube 23' having centrally arranged infrared receiver 11.

According to the embodiment of FIG. 2 a part of the totally reflecting boundary surface 1b', which has been symbolically illustrated, is shown in its immersed state in a medium which is to be monitored.

As further seen by referring to FIG. 2, the infrared radiation which is irradiated by the infrared transmitter 10, and schematically symbolized by the arrows, is deflected at the deflection cone 16 through an angle of about 90°. In the case of the presence of a liquid, and as shown at the left side of the illustration of FIG. 2, such infrared radiation is refracted at the boundary surface 1b into the denser medium and at that location absorbed. On the other hand, if the boundary surface 1b is located in air, as shown at the right-hand side of the hollow body probe 1', then the radiation S is deflected at the boundary surface 1b' and delivered by means of the infrared filter 14' with a further deflection at the optical lens 13 to the infrared receiver 11. The absorber tube 15 prevents penetration of non-defined radiation due to the scattered radiation into the receiving region of the infrared receiver 11.

Figure 3:
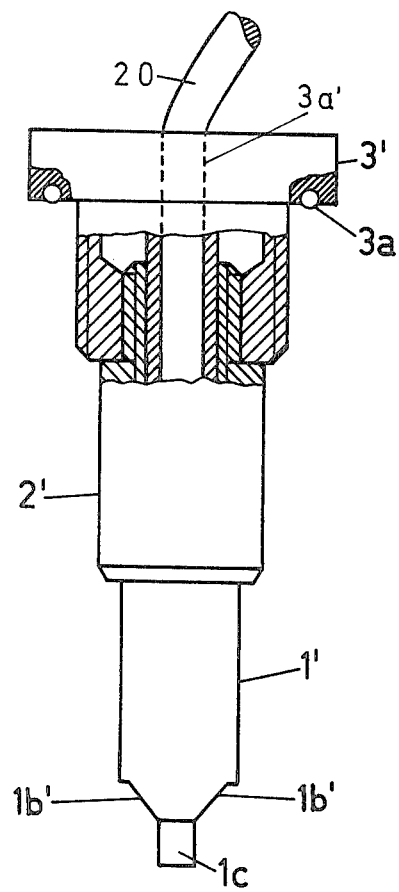
FIG. 3 illustrates an arrangement having a flat body as the carrier or support for a hollow body probe with a tapered portion or taper serving as a droplet catcher.

FIG. 3 illustrates an arrangement of an apparatus constructed according to the invention which can be directly installed in a flat body serving as a carrier or support. In the instant case such is a somewhat modified tank closure, which has been designated as a carrier or support 3' and has a sealing ring 3a for providing a sealing action at the side of the flange. In the embodiment under discussion the carrier or support 3' is fabricated of stainless steel and is equipped with a central bore 3a' for the throughpassage of the signal cable 20 needed for operation of the apparatus. A connection or connection element 2' fabricated of polychlorotrifluoroethylene (PCTFE) is threaded at its end face into the carrier 3' and, in the manner illustrated in FIG. 1, likewise threaded with a hollow body probe 1'. The hollow body probe 1' is fabricated from fluoroethylenepropylene (FEP), and, once again, will be seen to have totally reflecting boundary surfaces 1b' as well as an additional tapered portion or taper 1c, a so-called "droplet nose" which serves for the good flow-off of liquids.

Figure 3A:
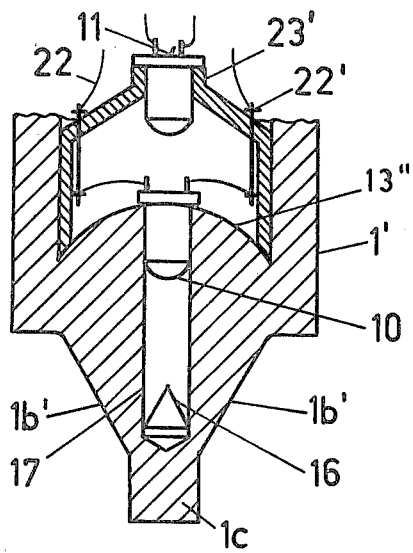
FIG. 3a is a sectional view showing in detail the tip of the hollow body probe of FIG. 3.

The hollow body probe 1' of FIG. 3, which is preferably fabricated according to injection molding techniques, has been shown in sectional view in FIG. 3a. Once again a deflection cone 16 serving for deflecting the radiation is located in a bore 17 and at the central region there is arranged a domed or arched surface for an infrared transmitter 10 of the previously mentioned type and which surface functions as an optical lens 13". The centering tube 23' together with its connections 22 and 22' will be seen to possess an essentially trapezoidal-shaped cross-sectional configuration and carries at its central region the infrared receiver 11.

The hollow body probe 1', shown in FIG. 3a, is especially suitable for mass production and renders superfluous the utilization of an optical lens 13 formed of glass or a Fresnel lens 13' which is temperature sensitive to a certain degree.

Figure 4:
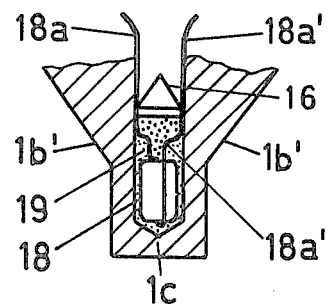
FIG. 4 illustrates in sectional view a heated tip of a hollow body probe.

The exemplary embodiment of apparatus shown in FIG. 4 is suitable for use with liquids having relatively high liquefying point.

In this arrangement there is provided a heating element 18, a PTC-resistor having its infeed lines 18a and 18a' embedded in a heat conducting molding or casting mass 19 and covered by a deflection cone 16. In this case the deflection cone 16 has a dual function: On the one hand, it deflects, as previously described, the transmitted radiation, and, on the other hand, it serves to radiate back the heat ascending from heating element 18, so that there is obtained an approximately uniform heating of the tapered portion 1c as well as the boundary surface 1b'.

Figure 4A:
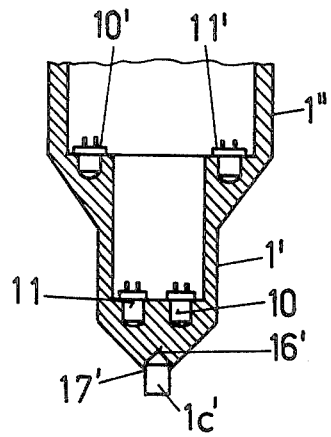
FIG. 4a is a schematical illustration of a heated tip having four heating elements.

Now in FIG. 4a there is illustrated in top plan view a hollow body probe 1 having four heating elements 18' connected in series and which are operated by a direct-current voltage of approximately 24 volts. These heating elements 18', again constituted by PTC-resistors, collectively form a temperature-stabilizing circuit which owing to its well known characteristics insures in a most simple manner for a uniform heating of the hollow body probe 1.

In special situations, for instance during employment in containers which are periodically sub-cooled, there could be connected at the terminals or connections designated by ± an electronic regulator or control.

Figure 5:
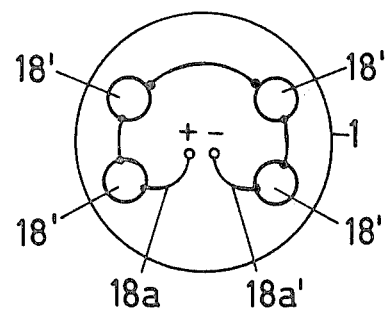
FIG. 5 illustrates a maximum-minimum circuit composed of two assembled together hollow body probes.

Now in the arrangement of FIG. 5 two hollow body probes 1' and 1" are assembled together into an apparatus. The infrared transmitters and infrared receivers which coact with one another in pairs have been designated by reference characters 10', 11' and 10, 11 respectively.

This arrangement which functions as a maximum-minimum circuit is to be designed in accordance with its geometric dimensions to a liquid level to be monitored or to a corresponding level difference. However, in order to be able to adjust the liquid level, in the present case the minimum level within certain limits, the tapered portion 1c' which functions as a drop or droplet nose, is to be constructed as a body which can be inserted from the outside and possesses at its tip confronting the infrared transmitter 10 and the infrared receiver 11 a deflection cone 16' which is formed by metalizing.

By appropriate selection of the depth of the bore 17' it is possible to adjust the level differences of the liquid to be monitored to accuracies within tenths of a millimeter. Of course the tapered portion or taper 1c' also can be designed in the form of a screw, so that at the location of installation, for instance in a tank structure, there would be possible a readjustment.

Depending upon the characteristics of the infrared transmitter and the infrared receiver there varies the angle enclosed by the boundary surfaces 1b, 1b'. In practice, angles between 30° to 120° have been found to be acceptable. Each of the exemplary embodiments herein discussed have an angle of 90°, as does also the cone angle of the deflection cones 16 and 16'.

For reasons of safety the infrared transmitter 10 is operated with minimum radiation output, in the embodiments under discussion at 15 to 30 mW/sterad. Especially when using halogen-containing polymerizates it is important that the infrared transmitters have as possible axial symmetrical radiation distribution. There could be determined as the optimum a spatial distribution of the radiation intensity in the plane of half power with a half angle aperture of less than 4°.

Basically, a multiplicity of synthetic, high molecular substances could be employed for the inventive apparatus. However, it has been found that for reasons of prolonged longevity of the apparatus, i.e., a longer period of use without revision or cleaning work being needed, there are required either substances of the same or related substance groups, especially for the hollow body probe and the connections to the support or carrier. The support or carrier itself can be, for instance, a steel pipe or tube, and an improvement can be achieved as concerns corrosion, particularly at the locations provided with threads if, however, for instance a protective hose composed of fluoroethylenepropylene is drawn over such type steel pipe-support.

Halogen-containing polymerizates which have been found to be particularly suitable for use with the inventive apparatus are, by way of example, fluoroethylenepropylene, perfluoroalkoxy, polychlorotrifluoroethylene, ethylene-chlorotrifluoroethylene, ethylene tetrafluoroethylene, polyvinyl fluoride and polyvinylidene fluoride, polytetrafluoroethylene, and so forth.

While there are shown and described present preferred embodiments of the invention, it is to be distinctly understood that the invention is not limited thereto, but may be otherwise variously embodied and practiced within the scope of the following claims. Accordingly,

What I claim is:

1. An electro-optical apparatus for the detection of the presence of a liquid, comprising:
   a hollow body probe composed of a synthetic, polymerized substance selected from a predetermined substance group and totally reflecting infrared radiation;
   at least one monochromatic infrared transmitter arranged at the region of said hollow body probe;
   at least one infrared receiver;
   a support having at least one hollow space;
   a detachable fluidtight connection means for connecting the hollow body probe with said support; and
   said detachable fluidtight connection means being composed of a synthetic, polymerized substance of the same substance group as the hollow body probe composed of said synthetic, polymerized substance.

2. The electro-optical apparatus as defined in claim 1, further including:
   circuit means for processing signals received from the infrared receiver.

3. The electro-optical apparatus as defined in claim 1, wherein:
   said support is provided at its outer surface with at least one layer composed of a synthetic, polymerized substance of the same substance group as the hollow body probe.

4. The electro-optical apparatus as defined in claim 1, wherein:
   said connection means comprises a sleeve having internal threads;
   said hollow body probe having external threads; and
   at least one of said threads having a substantially conically extending outer diameter.

5. The electro-optical apparatus as defined in claim 1, wherein:
   said connection means comprises a sleeve having internal threads;
   said hollow body probe having external threads; and
   at least one of said threads having a substantially conical-shaped extending core diameter.

6. The electro-optical apparatus as defined in claim 1, wherein:
   said support comprises a substantially tubular-shaped body containing said hollow space; and
   a signal cable receivable in said hollow space of said tubular-shaped body.

7. The electro-optical apparatus as defined in claim 1, wherein:
   said support comprises a substantially flat body containing said hollow space; and
   a signal cable receivable in said hollow space.

8. The electro-optical apparatus as defined in claim 1, wherein:
   said infrared transmitter and said infrared receiver are arranged adjacent one another.

9. The electro-optical apparatus as defined in claim 1, wherein:
   said hollow body probe includes totally reflecting boundary surface means;
   said infrared transmitter being arranged closer to said totally reflecting boundary surface means than said infrared receiver.

10. The electro-optical apparatus as defined in claim 9, further including:
    a deflection cone provided for said infrared transmitter at a side thereof where there is radiated the infrared radiation.

11. The electro-optical apparatus as defined in claim 9, wherein:
    said infrared transmitter has a side radiating infrared radiation; and
    an optical lens arranged forwardly of said radiating side of said infrared transmitter.

12. The apparatus as defined in claim 11, wherein:
    said optical lens comprises a Fresnel lens.

13. The apparatus as defined in claim 1, wherein:
    said hollow body probe contains a totally reflecting boundary surface means; and
    a tapered portion with which merges said totally reflecting boundary surface means.

14. The electro-optical apparatus as defined in claim 1, further including:
    an infrared filter arranged ahead of at least said infrared receiver.

15. The electro-optical apparatus as defined in claim 1, wherein:
    said infrared transmitter has a maximum radiation intensity amounting to less than about 200 mW/sterad;
    said infrared transmitter having an optical axis;
    the spatial radiation distribution of the infrared radiation having a main maximum which is at least approximately axially symmetrical and aligned essentially in the direction of the optical axis of the infrared transmitter; and
    the spatial distribution of the radiation intensity in a plane of half power has a half-angle aperture of less than 4°.

16. The electro-optical apparatus as defined in claim 1, wherein:
    said hollow body probe is composed of a halogen-containing polymerizate.

17. The electro-optical apparatus as defined in claim 16, wherein:
    said hollow body probe is formed of a substance selected essentially from the group consisting of: fluoroethylenepropylene, perfluoroalkoxy, polychlorotrifluoroethylene, ethylene-chlorotrifluoroethylene, ethylenetetrafluoroethylene, polyvinyl fluoride, polyvinylidene fluoride and polytetrafluoroethylene.

18. The electro-optical apparatus as defined in claim 1, wherein:
    said hollow body probe includes totally reflecting boundary surface means; and
    at least one heating element arranged at the region of said totally reflecting boundary surface means.

19. The electro-optical apparatus as defined in claim 18, wherein:
    said heating element constitutes a temperature-stabilizing circuit.

20. The electro-optical apparatus as defined in claim 1, wherein:
said infrared transmitter has a side which radiates infrared radiation; and
an absorber tube arranged about said infrared transmitter at least at the region of said side which radiates said infrared radiation.

21. The electro-optical apparatus as defined in claim 1, further including:
an additional hollow body probe; and
said hollow body probe and said additional hollow body probe defining two hollow body probes joined together to form a maximum-minimum circuit.

* * * * *